United States Patent [19]

Flegel et al.

[11] Patent Number: 4,512,923

[45] Date of Patent: Apr. 23, 1985

[54] LUTEINIZING AND FOLLICLE STIMULATING HORMONES AND PROCESS FOR THE PREPARATION THEREOF

[75] Inventors: Martin Flegel; Jan Pospisek; Josef Picha; Drahomira Pichova; Milan Krojidlo; Jiri Kolinsky, all of Prague, Czechoslovakia

[73] Assignee: SPOFA, spojene podniky pro zdravotnickou vyrobu, Prague, Czechoslovakia

[21] Appl. No.: 521,108

[22] Filed: Aug. 8, 1983

[30] Foreign Application Priority Data

Aug. 6, 1982 [CS] Czechoslovakia .................... 5868-82

[51] Int. Cl.³ .............................................. C07C 103/52
[52] U.S. Cl. .................... 260/112.5 LH; 260/112.5 R
[58] Field of Search ............... 260/112.5 R, 112.5 LH

[56] References Cited

U.S. PATENT DOCUMENTS 4,075,191  2/1978  Beddell et al. ............. 260/112.5 LH
4,101,537  7/1978  Nicolaides et al. ........ 260/112.5 LH
4,124,577  11/1978  Tinney et al. ............. 260/112.5 LH

*Primary Examiner*—Delbert R. Phillips
*Assistant Examiner*—F. T. Moezie

[57] ABSTRACT

A luteinizing and follicle stimulating hormone of the formula

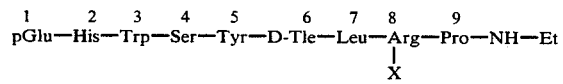

wherein X represents a hydrogen atom or a protective group is described. The described hormones evidence high gonadotropic activity and are useful in human and veterinary medicine.

2 Claims, No Drawings

LUTEINIZING AND FOLLICLE STIMULATING HORMONES AND PROCESS FOR THE PREPARATION THEREOF

This invention relates to luteinizing and follicle stimulating hormones and to a process for the preparation thereof. More particularly, the present invention relates to luteinizing and follicle stimulating hormones which are biologically active nonapeptides evidencing high gonadotropic activity which is of interest for use in both human and veterinary medicine, particularly in the control of estral cycles, the treatment of estral disturbances and as a nonsteroidal contraceptive.

The luteinizing and follicle stimulating (LH-FSH) described herein have releasing factor analogs of the formula

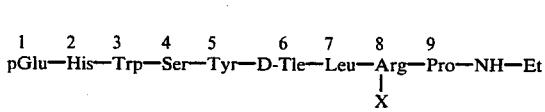

(1)

wherein X represents a hydrogen atom or a protective group, preferably a p-toluenesulfonyl (tosyl) radical. The remaining designations are those which are conventionally used, i.e., EX represents an ethyl group and the remaining symbols represent a binolent radical of the following compounds:

| pGlu | pyroglutamic acid, |
|---|---|
| His | histidine, |
| Trp | tryptophan, |
| Ser | serine, |
| Tyr | tyrosine, |
| D-Tle | 1-amino-3,3-dimethyl-D-Butanoic acid (tert-leucine) |
| Leu | leucine, |
| Arg | argine, and |
| Pro | proline. |

It has been known by those skilled in the art that the luteinizing and follicle stimulating hormone releasing factor (LRF) is produced by hypothalamus and induces the liberation of LH and FSH in the hypophysal anterior lobe. The liberated LH and FSH thus control the level of steroidal hormones in both humans and animals of both sexes. The LRF receptors have also been found in the area of the gonads. Agonistically (i.e., in the sense of releasing) active analogs are also found in human and veterinary medicine, namely, for the treatment of functional sterility and ovarian cysts. Furthermore, increased and prolonged action of certain LRF analogs may produce the reverse effect, i.e., the suppression of ovulation and spermatogenesis.

The natural LRF decapeptide of the formula

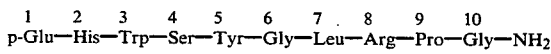

undergoes a rapid enzymatic degradation as a result of the cleavage of its p-Glu-His, Tyr-Gly and Pro-Gly bonds. Therefore, efforts were made, by different substitution of the amino acid radicals in these critical positions, to obtain more resistant analogs which would possess a modified or increased and prolonged action. Thus, the replacement of Gly in position 6 by different non-proteinogenous D-amino acid and their derivatives, especially of a certain lipophilic character, led the highly active agonistic substances, the simultaneous substitution of Gly-NH₂ in position 10 with convenient alkyl radicals produced, by virtue of a further increase in LRF activity, the so-called "super-active" analogs. The substances, when administered in low dosage, are of particular interest in the treatment of ovarial disturbances and for the induction of ovulation in the steered reproductive regime in dairy cows. High dosages of these agents may be used, for example, to control discontinuation of the estral cycle in farm animals, for nonsteroidal contraception and in the treatment of some endocrine-dependent tumors.

The continued systematic study of the structure-activity relations including novel structural alterations led to the development of LRF analogs with a high biological potency and potential therapeutic use. Thus, in accordance with the present invention, the glycine radical in position 6 of the natural LRF was replaced by a bivalent radical of a new amino acid of the D configuration which has not heretofore been described in this environment. This acid was the radical of 1-amino-3,3-dimethyl-D-butanoic acid (tert-leucine). The aliphatic side chain structure of this radical is considerably lipophilic and efficiently hindered from a sterical standpoint. Each of these characteristics has a favorable effect upon the biological properties of the LRF analogs, particularly in the degree and duration of their action. The resultant 6-D-Tle-LRF analog is presumed to be substantially more stable toward the metabolic effects and hence of more prolonged action than those analogs that contain an O-tert-butyl-D-serine radical or an aromatic side chain, such as 3-(2-naphthyl)-D-alanine. The 10-Gly-NH₂ was preferably replaced with NHEt.

Studies have revealed that the partially protected LRF analog precursors retain a substantive part of the activity of the respective unprotected compounds. Thus, the presence of a free Arg in position 8 is not crytical for high agnistic activity. This observation is of particular importance since it provides a possibility of producing the desired biological effect (especially in veterinary medicine) with the use of these synthetic precursors which are readily available and relatively inexpensive. Similar observations were previously reported in the opposite situation of certain LRF analogs having an inhibitory action.

The nonapeptide compounds of formula (1) can be prepared by processes which involve reactions combining the respective amino acids or lower peptide radicals with the use of preparative methods of peptide chemistry. A particularly useful process for this purpose involves combining a hexapeptide of the formula

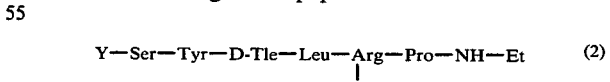

(2)

where X is defined as above and Y is selected from among a hydrogen atom or a hydrogenolytically removable protective group, preferably a benzyloxycarbonyl radical, with a reactive derivative of the tripeptide of formula

(3)

and, if required, removing the protective groups.

The described combining reactions may be effected either in solution as commonly employed in peptide chemistry (See E. Schroeder et al, The Peptides, Vol. I and II, Academy Press, New York 1965), or in solid phase (See J. M. Stewart et al, Solid Phase Peptides Synthesis, W. H. Freeman Comp., San Francisco, 1969). The temporary protection of the terminal amino groups is advantageously made by introduction of a benzyloxycarbonyl radical. The functional groups situated in the side chains (with the exception of Arg—need not be protected. Protection of the guanidino group of arginine is effected by means of a tosyl group. Although its elimination may be effected by conventional techniques, a novel procedure using a solution of trifluoromethanesulfonic acid in the presence of a suitable protective agent, such as thioglycolic acid, proved very effective. This technique ensures the rapid elimination of the tosyl group without the simultaneous deterioration of the remainder of the sensitive peptide molecule and, as a consequence, affords substantially higher yields of the desired product that an allowable by known techniques.

After spilling off the protective group, the resultant product may be purified immediately by liquid chromatography. This results in attainment of the nonapeptide of the invention in a state of high purity. The so-called reverse phase, i.e., silica gel (of 10–30 μm grain size) surface-modified by a chemically bound $C_8$–$C_{18}$ hydrocarbon layer is preferably used as a stationary phase. Elution may conveniently be effected with a mixture of methanol (20–60 volume percent dependent upon the peptide involved) and a 0.1 to 0.5%, preferably 0.2% aqueous trifluoroacetic acid as the mobile phase. The presence of trifluoroacetic acid as an ionization suppressant in the mobile phase is necessary in order to obtain efficient separation. This technique makes it possible to purify the substances in a single operation without the necessity of an additional desalting procedure.

Heretofore, liquid chromatography has not been used for the purification of similar peptide compounds. The described mobile phase was developed as an advantageous substitution for previously described module systems which employed buffer solutions of different pH values for the control of ionization of the processed substances. When these buffered mobile phases are employed, the separated products must be subjected to additional desalting which necessitates a time-consuming and laborious separation.

The invention will be more readily understood from the following exemplary embodiments which are set forth solely for purposes of exposition and are not to be construed as limiting. In the examples, Z represents a benzyloxycarbonyl group, Tos represents a tosyl (p-toluenesulfonyl) group and DCHA represents dicyclohexylamine.

EXAMPLE 1

Z—Pro—NH—Et

Fifty grams of Z-Pro (0.2 mole) were dissolved in 170 ml of dimethylformamide, then, 21 ml of pyridine were poured in and the solution cooled to −40° C. Next, pivalylchloride (29 ml, 0.22 mole) was added and the mixture stirred for 10 minutes at a temperature of −30° C. After cooling of the reaction mixture to −40° C., a solution of 10 g (0.21 mole) of ethylamine in 50 ml of dimethylformamide was added. After standing overnight at 0° C., the dimethylformamide was evaporated and the residue dissolved in ethyl acetate and allowed to crystallize. The yield was 50 g (91%) of the desired product, m.p. 125°–130° C.

EXAMPLE 2

Z-Arg(Tos)-Pro-NH-Et

Four and a half grams of Z-Pro-NH-Et (16.2 mmoles) were made free of the protective group by treatment with a hydrogen bromide solution in acetic acid. After standing at room temperature for 20 minutes, the hydrobromide was precipitated with ether and immediately dissolved in 30 ml of dimethylformamide.

Ten grams of Z-Arg (Tos) DCHA (17.8 mmoles) were decomposed with 2N HCl and the liberated Z-Arg (Tos) extracted into ethyl acetate. After evaporation of the solvent, this product was obtained in the form of a foam. The material was then dissolved in 60 ml of dimethylformamide and the solution cooled to −40° C. and treated at this temperature successively with 1.4 ml of pyridine (20 mmoles), 2.2 ml of N-ethylpiperidine and 2.1 ml of pivalylchloride (18 mmoles). After 20 min. of stirring at −30° C., the above mentioned solution of Pro-NH-Et HBr was poured in and the reaction mixture adjusted to a pH of 7.5 with N-ethylpiperidine and allowed to stand in a refrigerator overnight. The volatile portions were then evaporated, the residue extracted with ethyl acetate and the extract washed successively with 1N hydrochloric acid, 5% sodium hydrogen carbonate solution and water. The solvent was then distilled off under simultaneous azeotropical drying. The yield was 6.02 g (63%) of the desired product in the form of a foam. Amino acid composition analysis: Pro 0.91, Arg 1.09.

EXAMPLE 3

Z-Leu-Arg(Tos)-Pro-NH-Et

Six grams (8.7 mmole) of Z-Arg(Tos)-Pro-NH-Et were made free of the protective group with a hydrogen bromide solution in acetic acid. The hydrobromide was precipitated from the solution with ether and dissolved at once in 25 ml of dimethylformamide. The subsequent condensation was again performed by the above method of mixed anhydrides with the use of 3.72 g (8.7 mmoles) of Z-LeuDCHA, 1.2 ml (10 mmoles) of pivalylchloride, 0.83 ml (8.7 mmoles) of pyridine and 1.19 ml (8.7 mmoles) of N-ethylpiperidine, dimethylformamide being used as the solvent. The product was isolated in the same manner as described in example 2. The yield was 4.5 g (73%) of the desired product in the form of a foam. Amino acid composition analysis: Leu 0.98, Arg. 1.09, Pro 0.93.

EXAMPLE 4

Z-D-Tle-Leu-Arg(Tos)-Pro-NH-Et

Z-D-Tle DCHA (2.6 g, 5.82 mmoles) was treated with 0.1N sulphuric acid to decompose the salt and the liberated Z-D-Tle extracted into ethyl acetate. After evaporation of the solvent, 2 g of an oily product was obtained, the material being dissolved in 20 ml of methylenechloride.

Four grams (5.7 mmoles) of compound (3) were decarbobenzoxylated with hydrogen bromide in acetic acid. The product was liberated from the hydrobromide salt on an anion exchanger column in the OH⁻ cycle in a methanolic solution. The yield was 2.9 g of Leu-Arg (Tos)-Pro-NH-Et in the form of a foam. This product was homogeneous electrophoretically at a pH of 2.5 and 5.7 (detection with ninhydrin). The resultant free tripeptide amide was dissolved at once in 15 ml of methylenechloride and, on cooling to −20° C., the previously prepared Z-D-Tle solution and a solution of 2 g (9.7 mmoles) of dicyclohexylcarbodiimide in 10 ml of methylenechloride were added. The reaction mixture was allowed to stand in a refrigerator for 4 days. The dicyclohexylurea precipitate was then filtered off, the filtrate evaporated and the residue dissolved in ethyl acetate. The desired product was isolated as a neutral substance after repeated washing of the ethyl acetate solution successively with 1N hydrochloric acid, 5% sodium hydrogen carbonate solution and water. The yield was 3.9 g (93%) of the peptide in the form of a foam. The product was homogeneous chromatographically as checked on silica gel thin layer in a chloroform—methanol (9:1) system. Amino acid composition analysis: D-Tle 0.92, Leu 0.98, Arg 1.01, Pro 0.93.

EXAMPLE 5

Z-Ser-Tyr-D-Tle-Leu-Arg(Tos)-Pro-NH-Et

Compound (4) (3.6 g) was made free of the protective group by hydrogenolysis on a Pd catalyst. A yield of 3.0 g (4.4 mmoles) of the free tetrapeptide was obtained. The fragment condensation with Z-Ser-Tyr-N$_3$ was performed in an anhydrous dimethylformamide—methylenechloride mixture at −30° C. with the use of 1.9 g of Z-Ser-Tyr-N$_2$H$_3$, 1.5 ml of an 8N hydrogen chloride solution in dioxan and 0.9 ml of n-butyl nitrite. The neutralization (to pH 8) was made with N-ethylpiperidine. The reaction mixture was then allowed to stand in a refrigerator at 0° C. for 3 days. The volatile portions were evaporated and the residue dissolved in ethyl acetate. The solution was repeatedly washed successively with 1N hydrochloric acid, a 5% sodium hydrogen carbonate solution and water, and then dried and evaporated. The yield was 4.14 g (76%) of the noncrystalline hexapeptide. The product was homogeneous chromatographically as checked by liquid chromatography (0.4×25 cm column size, stationary phase: modified silica gel, mobile phase: 70 vol.% of methanol and 30 vol.% of a phosphate buffer, pH 4.4). The product contained 82% of the desired hexapeptide; amino acid composition analysis: Ser 1.14, Tyr 1.05, D-Tle 0.98, Leu 1.03, Arg 1.04, Pro 1.00.

EXAMPLE 6 pGlu-His-Trp-Ser-Tyr-D-Tle-Leu-Arg(Tos)-Pro-NH-Et 3.8 grams of the hexapeptide of example 5 was made free of the protective group by hydrogenolysis on a Pd catalyst in a methanolic solution. A yield of 3.2 g of the substance containing 88% of the free hexapeptide (determined by liquid chromatography, the column size and the stationary phase as above, mobile phase: 50 vol.% of methanol and 50 vol.% of a trifluoroacetic acid—triethylamine buffer, pH 3.9, detection in ultraviolet at 220 nm) was obtained.

Azide condensation was performed in an anhydrous dimethylformamide—dimethylsulfoxide (1:1) mixture with the use of 1.6 g of PGlu-His-Trp-N$_2$H$_3$, 3.2 g of the preceding hexapeptide and 0.5 ml of n-butyl nitrite; the reaction taking place at −20° C., and the azide formation: after 30 min. at the same temperature. The reaction mixture was then adjusted to a pH of 8–9 and left in a refrigerator for 4 days with intermittent checking of pH. After evaporation of the solvents, the residue was dissolved in a small volume of ether and the resultant oily solution diluted with 30 ml of methanol. The product was precipitated by the addition of ethylacetate, collected on a filter and washed with an ethyl acetate—ether mixture. The yield was 3.65 g (87%) of the crude nonapeptide. As shown by liquid chromatography (the column size and the stationary phase as above, mobile phase: 60 vol.% of methanol and 40 vol.% of a phosphate buffer of pH 7.0, detection in ultraviolet at 210 nm), the resultant product contained 70% of the desired nonapeptide and, in addition to this, a certain amount of the starting compounds, as evidenced by the corresponding chromatographic peaks (identification by mixed feed with standards) and by the amino acid composition analysis of the crude nonapeptide Glu 1.43, His 1.41, Trp 1.10, Ser 1.09, Tyr 1.20, D-Tle 0.89, Leu 1.00, Arg 0.88, Pro 0.90.

For the evaluation of the biological activity, the substance was purified by preparative chromatography under the following conditions: column size 2.5×30 cm, stationary phase: modified silica gel (grain size 10 um), mobile phase: 60 vol.% of methanol and 40 vol.% of a 0.2% aqueous trifluoroacetic acid, detection at 210 nm. a sample (300 mg) of the crude nonapeptide material (injected in 3 ml of the mobile phase) yields 148 mg of a product of 96° purity. Its amino acid composition analysis: Glu 1.01, His 1.01, trp 0.90, Ser 0.95, Tyr 1.01, D-Tle 0.95, Leu 1.00, arg 0.99, Pro 1.01.

EXAMPLE 7 pGlu-His-Trp-Ser-Tyr-D-Tle-Leu-Arg-Pro-NH-Et 30 milligrams of the compound of example 6 was purified as above and dissolved in 0.6 ml of trifluoroacetic acid. Thioglycolic acid (0.5 ml) was added and the mixture cooled to 0° C., treated with 0.4 ml of trifluormethanesulphonic acid and allowed to stand for 30 minutes in a refrigerator. The product was then precipitated with ether and collected on filter. The resultant moderately hygroscopic powder was dissolved in 1M acetic acid and the solution freeze-dried. A yield of 25 mg of the crude product was obtained. The material was purified by liquid chromatography on a 2.5×30 cm column with the use of modified silica gel as the stationary phase and a mixture of 55 vol.% of 45% aqueous methanol and 45 vol% of 0.2% aqueous trifluoroacetic acid as the mobile phase. A sample (25 mg) of the purified material was dissolved in 0.5 ml of the mobile phase and injected, the record being taken at 280 nm. The fractions containing the pure desired product were combined and the methanol evaporated under reduced pressure at 30° C. The purified product was obtained in a yield of 10.5 mg and with 98% purity by freeze-drying of a solution in 1M acetic acid. Amino acid composition analysis: Glu 1.03, His 0.94, Trp 0.80, ser 0.95, Tyr 0.96, D-Tle 0.90, Leu 0.99, arg 1.06, Pro 1.01.

The LRF analogs of examples 6 and 7 were administered intravenously to ovariectomized heifers in doses of 10 and 200 mg. An RIA assay was made in a homolog system of double antibodies (R. Stupnicki et al,: Endocrinology 68, 6, 1976. The bovine NIH-LER-1716-2 preparation was then used as the iodination standard, the RIA sensitivity being greater than 100 mg. The STH prolactin cross reaction was 1%. The test results are set forth in Table 1, below:

Levels of LH+FSH after the administration of 200 µg of LRF and analogs

| Compound | FS action onset min. | duration min. | average ∅ FSH concentration μg/ml |
|---|---|---|---|
| blank | — | — | 31,2 ± 1,9 |
| LRF | 40 ± 11,5 | 100 ± 26,7 | 108,4 ± 16,1 |
| Ex. 6 | 26,7 ± 3,8 | 43 ± 20,4 | 72,4 ± 10,9 |
| Ex. 7 | 40,0 ± 6,0 | 230 ± 32,1 | 110,9 ± 11,7 |

| Compound | lut. action onset min. | duration min. | average ∅ LH concentration μg/ml |
|---|---|---|---|
| blank | — | — | 0,26 ± 0,04 |
| LRF | 53,3 ± 13,9 | 12,3 ± 5,0 | 7,43 ± 1,6 |
| Ex.6 | 46,6 ± 15,4 | 86,7 ± 10,7 | 3,88 ± 1,3 |
| Ex. 7 | 53,3 ± 19,0 | 236,7 ± 10 | 11,24 ± 1,59 |

The compound of example 7 when administered at the two dosage levels evidenced a markedly pronounced agonistic effect. This compound was found to be more active than the compound of example 6, that is, the corresponding tosyl derivative, and far more active than the natural LRF, which served as a reference compound for comparison. The replacement of Gly by D-Tle in accordance with the invention resulted in a remarkable increase both in the degree and duration of the LRF action. This effect was observed distinctly even at a dosage of 10 mg per animal. The partially protected precursor of example 6 was found to possess considerable activity. This finding confirmed the significant effect of the noted structural alteration in position 6 on the conformation (sterical arrangement) of the peptide molecule. The favorable effect of his replacement was predominant over the adverse effect of the tosylation of Arg in position 8. The corresponding 8-tosyl derivative of the natural LRF was almost inactive.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. Luteinizing and follicle stimulating hormone, capable of releasing factor analogs of high gonadotropic activity, of the formula

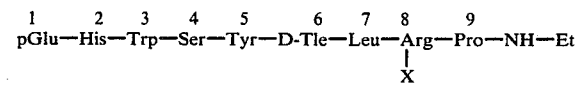

wherein X is selected from the group consisting of a hydrogen atom and a protective group.

2. Hormone in accordance with claim 1 wherein the protective group is a p-toluene-sulfonyl radical.

* * * * *